United States Patent [19]

Kato et al.

[11] Patent Number: 4,507,234

[45] Date of Patent: Mar. 26, 1985

[54] CONJUGATE HAVING CYTOTOXICITY AND PROCESS FOR THE PREPARATION THEREOF

[75] Inventors: Yoshinori Kato; Naoji Umemoto, both of Hino; Masahiko Saito, Saitama; Takeshi Hara, Hachioji, all of Japan

[73] Assignee: Teijin Limited, Osaka, Japan

[21] Appl. No.: 563,860

[22] Filed: Dec. 21, 1983

[30] Foreign Application Priority Data

Dec. 24, 1982 [JP] Japan ................................ 57-226236

[51] Int. Cl.³ ...................... C07G 7/00; C07C 103/52; C08L 89/00; A61K 39/44
[52] U.S. Cl. ................................ 260/121; 260/112 B; 424/85; 514/2
[58] Field of Search .............. 260/121, 112 B; 424/85, 424/177

[56] References Cited

U.S. PATENT DOCUMENTS 4,046,722  9/1977  Rowland ........................ 260/112 B Primary Examiner—Howard E. Schain
Attorney, Agent, or Firm—Sughrue, Mion, Zinn, Macpeak and Seas

[57] ABSTRACT

A conjugate having cytotoxicity prepared by covalently binding a serum albumin having cytotoxic substance linked thereto to an immunoglobulin, or its fragment, which is able to bind selectively with a particular antigen of cells to be killed.

10 Claims, No Drawings

CONJUGATE HAVING CYTOTOXICITY AND PROCESS FOR THE PREPARATION THEREOF

BACKGROUND OF THE INVENTION

1. Field of the Invention

The present invention relates to a novel conjugate having cytotoxicity and a process for the preparation thereof. More particularly, the present invention relates to a novel conjugate having cytotoxicity comprising a constituent part consisting of an immunoglobulin capable of binding selectively to a particular antigen possessed by a cell to be killed (hereinafter referred to as a target cell) or consisting of its fragment having a part which binds to such antigen and a constituent part consisting of a serum albumin having a cytotoxic substance linked thereto and a process for the preparation of such a conjugate. The conjugate having cytotoxicity obtained according to the present invention is useful, for instance, as an antitumor agent which exerts an action on cancer cells selectively.

2. Description of the Prior Art

Studies and attempts have hitherto been made to bind cytotoxic substances of various kinds to an immunoglobulin, which is capable of binding selectively to a target cell, with the purpose of destroying certain kinds of cells selectively. For instance, a conjugate comprising an immunoglobulin having p-bis(2-chloroethyl)amino-L-phenylalanine, etc. linked thereto (Japanese Patent Application Laid-open No. 61640/76), a conjugate comprising an immunoglobulin having methotrexate linked thereto (Japanese Patent Application Laid-open No. 65829/81), a conjugate comprising an immunoglobulin having chlorambucil, etc. linked thereto (Japanese Patent Application Laid-open No. 65828/81), a conjugate comprising an immunoglobulin having mitomycin C, etc. linked thereto (Japanese Patent Application Laid-open No. 92325/80), and a conjugate comprising an immunoglobulin having daunomycin linked thereto (Japanese Patent Application Laid-open No. 144723/76) are known.

These conjugates having cytotoxicity obtained according to the abovementioned methods are expected to bind selectively to a cancer cell and exert a toxic action on the cancer cell and accordingly may be regarded as very useful conjugates. However, in case where the cytotoxic substance is directly bound to the antibody, if a large amount of cytotoxic substances is bound to the immunoglobulin, the activity of the antibody to recognize the antigen tends to become low. Therefore, only a small amount of cytotoxic substance has to be bound to the antibody to avoid such a problem.

SUMMARY OF THE INVENTION

As the result of an elaborate study to obviate such defects of the prior art, the inventors of the present invention have found out that a conjugate of cytotoxic substance and immunoglobulin having a large amount of cytotoxic substance linked thereto without damging the activity of the antibody to recognize the antigen can be obtained by first making a large amount of a cytotoxic substance bind to serum albumin and then by binding said serum albumin, which has a cytotoxic substance linked thereto, to an immunoglobulin or its fragment, thus achieving the present invention.

The present invention is directed to a conjugate having cytotoxicity prepared by covalently binding a serum albumin having a cytotoxic substance linked thereto to an immunoglobulin, or its fragment, which is able to discriminately bind to a particular antigen of a cell to be killed, and a process for the preparation thereof.

DESCRIPTION OF THE PREFERRED EMBODIMENTS

In the present invention, an immunoglobulin (guiding part of a conjugate having cytotoxicity) which is capable of discriminately binding to a particular antigen possessed by a cell to be killed includes the following. It is an immunoglobulin prepared from antisera isolated from a man or animals such as a monkey, horse, cow, goat, sheep, rabbit, guinea pig, hamster, rat, mouse, etc., which are immunized with such target cells as tumor cells or certain lymphocytes or tissues which contain any of them, by such a publicly known method as ethanol fractionation, ammonium sulfate fractionation, ion exchange, and gel filtration column chromatography; or a monoclonal antibody obtained from an immortalized cell prepared by cancerating antibody-producing cells collected from a man or an animal, which is immunized with the target cells, with the use of a carcinogen or from a hybridoma prepared by fusing them with myeloma cells. An immunoglobulin, which is obtained by cleaving its binding to the target cell by use of a surface active agent, etc. and is specific to said target cell, is also included in the immunoglobulins of the present invention.

It is known that the immunoglobulin falls into five classes, i.e. IgG, IgA, IgM, IgD, and IgE, and that some of them consist of several subclasses. But they are commmon in their basic structure in that they consist of two heavy chains and two light clains and that they are composed of Fab moieties which have an activity of binding to an antigen and an Fc moiety which has an effector activity. However, IgM exists as a pentamer and IgA partially as a dimer.

As a guiding part of the conjugate having cytotoxicity, and whole of the immunoglobulin may be used and its fragment may also be used so far as the fragment contains its antigen binding part. As such antibody fragment, monomeric IgMs of IgM antibody and a fragment having no Fc part of the antibody, for instance, are used. IgMs is obtained, for instance, by reducing IgM with cysteine. IgMs has a special feature in that a thiol functional group, which arises from a disulfide group linking IgMs to each other in the original IgM, can be used in linking IgMs to albumin, and also in that IgMs is rather desirable to be used for preparing a stable conjugate having less tendency to aggregate as compared with IgM. In the conjugate, which contains an Fc part in it, the Fc part induces the indiscriminate adsorptive binding to cells other than target cells and also the binding to Fc receptor on the cell membrane, thus reducing the capability of the conjugate having cytotoxicity to select cells to be killed. Furthermore, since the antigenicity of the immunoglobulin as a xenogeneic protein is especially strong at its Fc part, a fragment of the immunoglobulin having no Fc part is preferable to be used as a guiding part of the conjugate having cytotoxicity from a viewpoint of lowering the antigenecity of the conjugate protein. The decomposition of an immunoglobulin with a proteolytic enzyme such as papain, trypsin, chymotrypsin, plasmin, etc. generally gives what is called Fab fragment having one variable region. Also the peptic decomposition, or the tryptic decomposition depending upon the conditions, of an immunoglobulin gives what is called F(ab')2 fragment having two variable regions. This fragment further turns to monovalent Fab' fragments when it is treated with a mercaptan. When the immunoglobulin is decomposed while being denatured, it gives the variable region only. The immunoglobulins and the abovementioned fragments arising from immunoglobulins can all be used as a guiding part of the protein conjugate of the present invention disregard of the class and subclass to which the material globulins belong.

Another constituent part of the hybrid having cytotoxicity of the present invention is a serum albumin with a cytotoxic substance bound thereto. As a serum albumin which is to function as a carrier to support a cytotoxic substance, serum albumins of man and various animals are used and, of them, those of man and cow are especially desirable. As cytotoxic substances to be bound to the serum albumin, for instance, anticancer drugs of various kinds can be used, and especially desirable ones are those anticancer drugs or derivatives thereof which have a group capable of reacting with and binding to an amino group of the serum albumin. As concrete examples, the following compounds expressed by the respective formulas can be mentioned, but not to be limited to them.

Nitrosourea derivatives

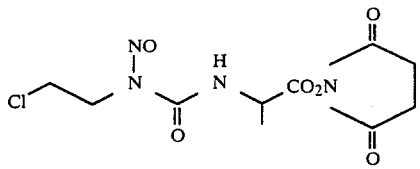

Chlorambucil derivatives

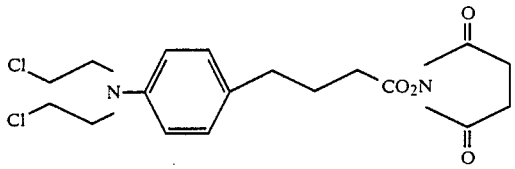

Mitomycin C derivatives

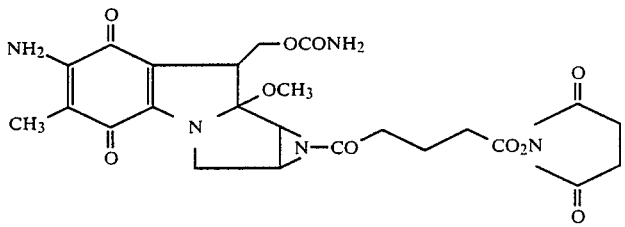

Daunomycin derivatives

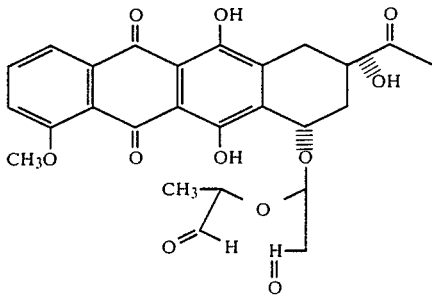

5-Fluoro-2'deoxyuridine derivatives

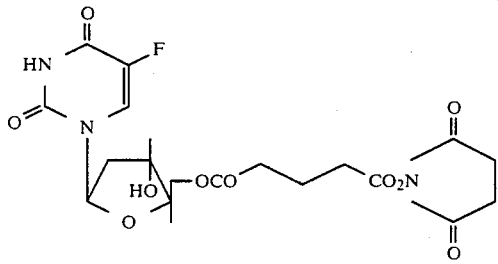

Desacetylvinblastic acid azide derivatives

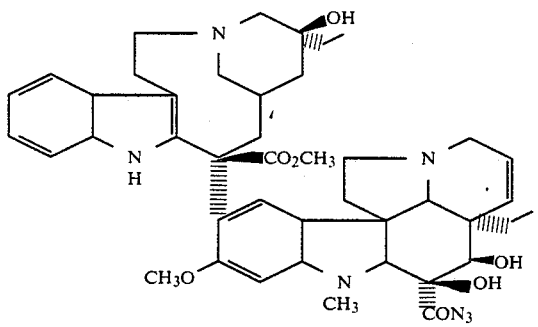

Methotrexate active ester derivatives

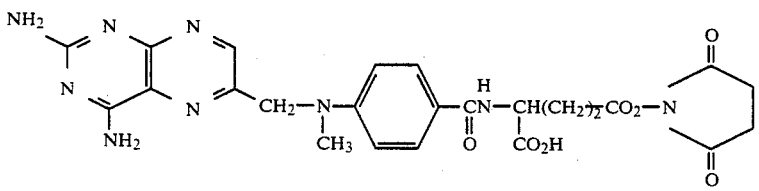

Actinomycin D oxazinone derivatives

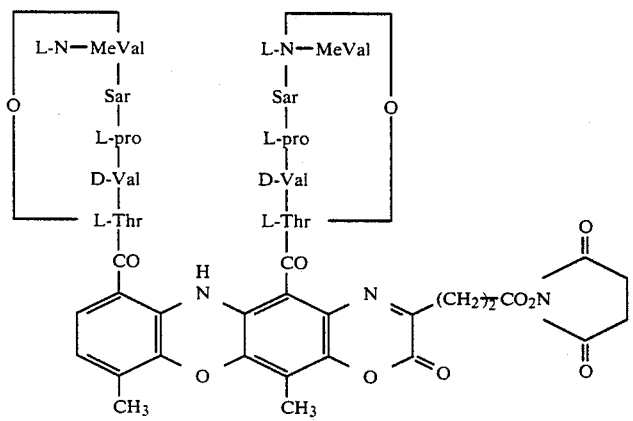

Of the conjugates having cytotoxicity of the present invention obtained by covalently linking a serum albumin having a cytotoxic substance linked thereto to an immunoglobulin or its fragment, the conjugates expressed by the following formula (I) are desirable from the viewpoint of their preparation, purification, and activity, $$Ab-B_1-S_1-Al-NH-Cy)_m)_n \qquad (I)$$

wherein Ab indicates an immunoglobulin or its fragment, Al a serum albumin, and Cy a cytotoxic substance respectively. $S_1$ and NH indicate a sulfur atom and an imino group in the serum albumin respectively. $B_1$ indicates a divalent organic group. m indicates an integer 1 to 30 and n an integer 1 to 10.

Of these conjugates mentioned above, the conjugates expressed by the following formula (II) or (III) are especially desirable $$Ab-(B_2)t_2-S_2-(B_3)t_3-S_1-Al-NH-Cy)_m)_n \qquad (II)$$

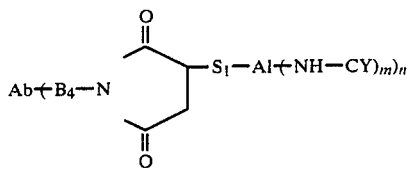  (III)

wherein definitions of Ab, Al, Cy S, NH, m, and n are the same as those given in case of formula (I). $S_2$ indicates a sulfur atom. $B_2$, $B_3$, and $B_4$ are divalent organic groups. $t_2$ and $t_3$ are identical with or different from each other, being 0 or 1.

In the above formula (II), when $t_2=0$, $S_2$ is a sulfur atom arising from the immunoglobulin or its fragment and when $t_2=1$, $S_2$ is a sulfur atom introduced by the cross-linking agent. In said formula (II), when $t_3=0$, the sulfur atoms $S_1$ and $S_2$ are directly linked together to form a disulfide group giving the conjugates expressed by the following formula (II-1)

$$Ab—(B_2)t_2—S_2—S_1—Al—NH—Cy)_m)_n \quad (II-1)$$

wherein definitions of Ab, Al, Cy, $S_1$, NH, m, and n are the same as those given in case of formula (I), and definitions of $S_2$, $B_2$, and $t_2$ are the same as those given in case of formula (II).

In the above formula (II), when $t_3=1$, the sulfur atoms $S_1$ and $S_2$ are linked together through a divalent organic group $B_3$ giving the conjugates expressed by the following formula (II-2)

$$Ab—(B)t_2—S_2—B_3—S_1—Al—NH—Cy)_m)_n \quad (II-2)$$

wherein definitions of Ab, Al, Cy, $S_1$, NH, m, and n are the same as those given in case of formula (I), and definitions of $S_2$, $B_2$, $B_3$ and $t_2$ are the same as those given in case of formula (II).

In the above formulas (II) and (II-2), $B_3$ is a cross-linking agent having 2 functional groups which react with thiol groups, for instance, a cross-linking agent expressed by the following formula (IX), or a divalent organic group arising from benzoquinone,

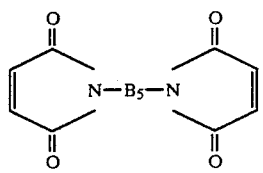  (IX)

wherein $B_5$ is a divalent organic group. $B_2$ in the formula (II) is a divalent organic group arising from cross-linking agents such as a cross-linking agent expressed by the following formula (X)

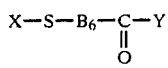  (X)

wherein X is as defined hereinafter with regard to the formula (V). $B_6$ indicates a divalent organic group and Y is an alcohol rest of an active ester:
a cross-linking agent expressed by the following formula (XI)

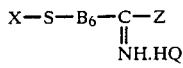  (XI)

wherein X is as defined with regard to the formula (V) and definition of $B_6$ is same as that given in case of formula (X). Z indicates an alcohol rest of an imido ester and Q indicates a halogen atom:
a cross-linking agent (2-iminothiolactone) expressed by the following formula (XII)

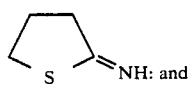  (XII)

and a cross-linking agent (N-acetyl homocystine) expressed by the following formula (XIII)

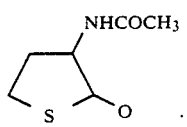  (XIII)

To give concrete examples of monovalent organic groups with are capable of forming an active disulfide group together which a linked sulfur atom, 2-pyridylthio group

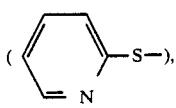

4-pyridylthio group

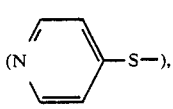

3-carboxy-4-nitrophenylthio group

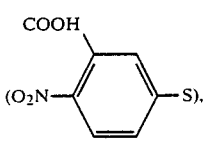

4-carboxy-2-pyridylthio group

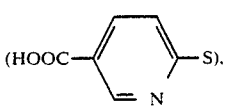

N-oxy-2-pyridylthio group

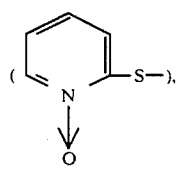

2-nitrophenylthio group

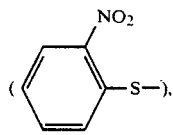

4-nitro-2-pyridylthio group

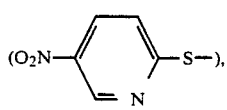

2-benzothiazoylthio group

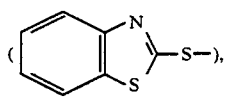

2-benzoimidazoylthio group

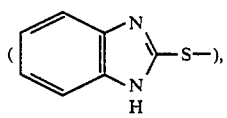

and N-phenylamino-N'-phenyliminomethylthio group

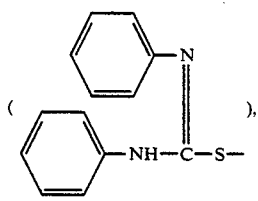

for instance, may be mentioned.

Though no specific limit is placed upon said divalent organic group expressed by $B_5$ or $B_6$ so far as it is chemically inert, it may be freely chosen from among alkylene groups which have or have not branching(s), phenylene groups, etc., in general. By way of concrete example of the alcohol rest of an active ester expressed by Y, 2,4-dinitrophenoxy group

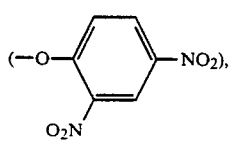

succinimidoxy group

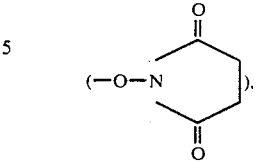

etc. may be mentioned. As an example of the alcohol rest of imidoester expressed by Z, methoxy group, ethoxy group, etc. may be mentioned. As an example of the halogen atom expressed by Q, chlorine, bromine, etc. may be mentioned.

To mention concrete examples of said cross-linking agent, there are cross-linking agents expressed by formula (IX) such as N,N'-(1,2-phenylene)dimaleimide

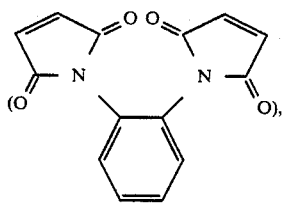

N,N'-(1,4-phenylene)dimaleimide

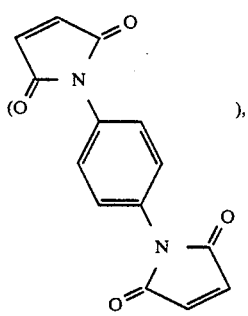

4,4'-bis(maleoylamino)azobenzene

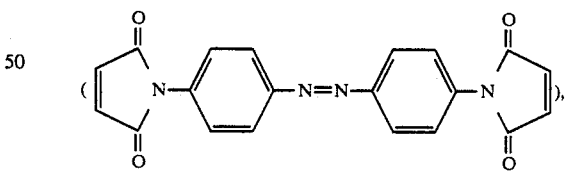

bis(N-maleimidomethyl)ether

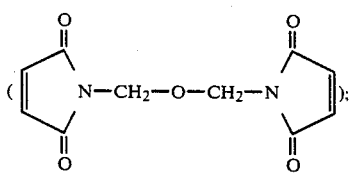

cross-linking agents expressed by formula (X) such as N-succinimidyl 3-(2-pyridyldithio)propionate and N-succinimidyl 3-(2,4-dinitrophenoxy)butylate; and cross-linking agents expressed by formula (XI) such as methyl 3-(2-pyridyldithio)propionimidate hydrochloride.

In the aforementioned formula (III), $B_4$ is a divalent organic group, expressed by the following formula (XIV), arising from a cross-linking agent having a maleimide group

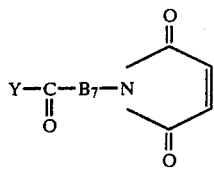 (XIV)

wherein Y has the definition given earlier in formula (X) and $B_7$ is a divalent organic group.

The divalent organic group expressed by $B_7$ has no specific limit placed upon it, so far as it is chemically inert; it may be freely chosen from among alkylene groups, phenylene groups, etc. which have or have not branching(s).

As concrete examples of the cross-linking agent expressed by formula (XIV), meta-(N-maleimido)benzoic acid N-hydroxysuccinimide ester

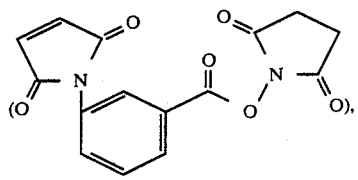

meta-(N-maleimido)benzoic acid 2,4-dinitrophenylester, β-(N-maleimido)propionic acid N-hydroxysuccinimido ester, etc. may be mentioned.

The conjugate having cytotoxicity of the present invention can be prepared by covalently binding a serum albumin having a cytotoxic substance linked thereto to an immunoglobulin or its fragment. More particularly, of the conjugates having cutotoxicity of the present invention, a conjugate expressed by the formula (II-1) can be prepared by reacting a serum albumin expressed by the following formula (V) having an active disulfide group having a cytotoxic substance linked thereto $XS_1-Al-NH-Cy)_m$ (V)

wherein Al, Cy, $S_1$, NH and m are as defined with regard to the formula (I) and X indicates a group which is capable of forming an active disulfide linkage with a neighboring sulfur atom:
with an immunoglobulin or its fragment expressed by the following formula (IV) having a generated or introduced thiol group $Ab-(B_2)t_2-S_2H)_{n'}$ (IV)

wherein Ab is as defined with regard to formula (I); definitions of $S_2$, $B_2$, and $t_2$ are the same as those given in case of formula (II); and n' is an integer 1 to 10; or by reacting a serum albumin expressed by the following formula (VII) having a cytotoxic substance linked thereto $HS_1-Al-NH-Cy)_m$ (VII)

wherein Al, Cy, $S_1$, NH and m are as defined with regard to the formula (I);
with an immunoglobulin or its fragment expressed by the following formula (VI) having an induced or introduced active disulfide group $Ab-(B_2)t_2-S_2X)_{n'}$ (VI)

wherein Ab is as defined with regard to formula (I); $S_2$, $B_2$, and $t_2$ are as defined in case of formula (II); n' is as defined in case of formula (IV); and X is as defined with regard to formula (V):

In the aforementioned formula (IV), when $t_2=0$, the immunoglobulin or its fragment expressed by formula (IV) is either an immunoglobulin or its fragment having a thiol group of its own as represented by monomeric IgMs obtained from IgM and, Fab' or an immunoglobulin or its fragment having a thiol group generated from the disulfide group. The immunoglobulin or its fragment expressed by formula (IV), wherein $t_2=1$, having a thiol group can be prepared either by allowing an immunoglobulin or its fragment to react with a cross-linking agent expressed by said formula (X) or (XI), followed by the reduction reaction in which a thiol group is generated from the introduced active disulfide group, or by allowing an immunoglobulin or its fragment to react with a cross-linking agent expressed by said formula (XII) or (XIII).

In case where $t_2=0$ in the aforementioned formula (VI), the immunoglobulin or its fragment having such an active disulfide group can be prepared by subjecting an immunoglobulin or its fragment having its own or generated thiol group to the action of an active disulfide group-introducing agent.

As the active disulfide compounds which can be used for the abovementioned purpose, 2-pyridyldisulfide

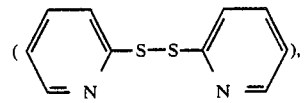

4-pyridyldisulfide

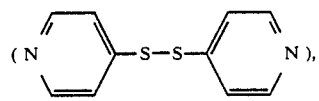

5,5'-dithiobis(2-nitrobenzoic acid)

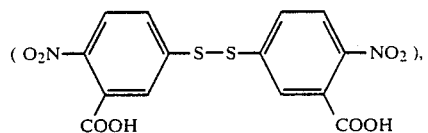

4-carboxy-2-pyridyldisulfide

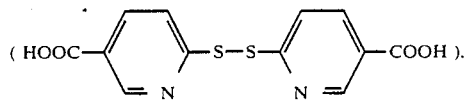

N-oxy-2-pyridylsulfide

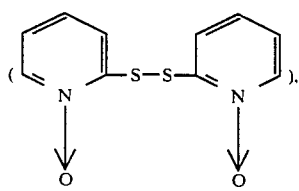

2-nitrophenyldisulfide

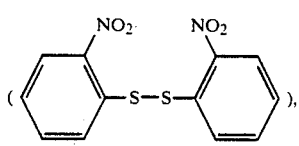

4-nitro-2-pyridyldisulfide

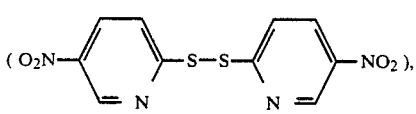

2-benzothiazoyldisulfide

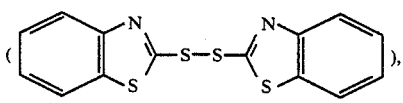

2-benzoimidazoyldisulfide

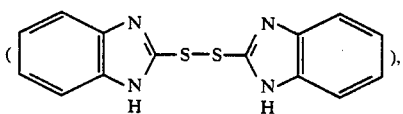

and N-phenylamino-N'-phenyliminomethyldisulfide

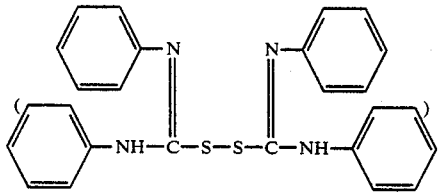

may be mentioned.

When the disulfide linkage at the hinge region of the aforementioned F(ab')$_2$ is cleared by sulfonation with the use of sulfite ion, Fab' having an S-sulfo group (—S—SO$_3^-$) in the molecule can be obtained. This Fab' favorably reacts with a serum albumin expressed by formula (VII) having a cytotoxic substance linked thereto to form a conjugate having cytotoxicity expressed by formula (II-1).

A process for the preparation of a serum albumin expressed by formula (V) or formula (VII) having a cytotoxic substance linked thereto will be described later.

Of the conjugates having cytotoxicity of the present invention, a conjugate expressed by formula (II-2) can be prepared by binding a serum albumin expressed by said formula (VII) having a cytotoxic substance linked thereto to an immunoglobulin or its fragment expressed by said formula (IV) having a generated or introduced thiol group with the use of a cross-linking agent having 2 functional groups which are able to react with thiol groups. It is desirable to carry out the abovementioned process in a two-step reaction. In the first step, either an immunoglobulin or its fragment expressed by formula (IV) having a generated or introduced thiol group or a serum albumin expressed by formula (VII) having a cytotoxic substance linked thereto is allowed to react with an excess of the cross-linking agent, for instance, expressed by formula (IX), followed by the purification of the obtained intermediate product. In the second step, thus obtained intermediate product is made to react with the other of the proteins. By following the abovementioned reaction procedures, the desired conjugate having cytotoxicity expressed by formula (II-2) can be obtained.

Further, of the onjugates having cytotoxicity of the present invention, a conjugate expressed by formula (III) can be prepared, for instance, by reacting a serum albumin expressed by the abovementioned formula (VII) having a cytotoxic substance linked thereto with an immunoglobulin or its fragment expressed by the following formula (VIII) having an introduced maleimide group

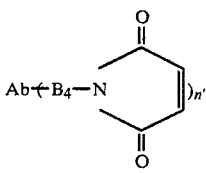

(VIII)

wherein definition of Ab is the same as that given in case of formula (I); n' has the meaning given in case of formula (IV); and B$_4$ is as defined with regard to formula (III).

The immunoglobulin or its fragment expressed by said formula (VIII) having an introduced maleimide group can be prepared, for instance, by making an immunoglobulin or its fragment react with a cross-linking agent expressed by said formula (XIV) having a maleimide group.

Next, an explanation will be made hereunder as to the process of preparing a serum albumin expressed by said formula (V) or formula (VII) having a cytotoxic substance linked thereto. There are various processes for the preparation of such serum albumin having a cytotoxic substance linked thereto and one of them will be described as an example in the following.

First, a thiol group of the serum albumin is allowed to react with such an active disulfide compound as 2-pyridyldisulfide, 4-pyridyldisulfide, etc., which are referred to as an example in the paragraph relating to the process for the preparation of an immunoglobulin or its fragment expressed by the aforementioned formula (VI) having an active disufide group, to obtain a serum albumin expressed by the following formula (XV) having an active disulfide group $XS_1—Al$ (XV)

wherein definitions of Al, and $S_1$ are same as those given in case of formula (I) and definition of X is same as that given in case of formula (V).

A appropriate cytotoxic substance is then made to react with the obtained serum albumin to have the cytotoxic substance linked to amino groups of the albumin, thus obtaining a serum albumin expressed by the aforementioned formula (V) having an active disulfide group and having the cytotoxic substance linked thereto. Derivatives of serum albumin expressed by the aforementioned formula (VII) can be obtained by treating the derivatives of albumin expressed by the aforementioned formula (V) having an active disulfide group, which is obtained according to the above procedure, with 2-mercaptoethanol or dithiothreitol.

A process for the preparation of a conjugate having cytotoxicity is explained by example in the following.

(1) A method in which a serum albumin expressed by formula (V) having an active disulfide group and having a cytotoxic substance linked thereto is allowed to react with an immunoglobulin or its fragment expressed by formula (IV) having a generated or introduced thiol group, or in which a serum albumin expressed by formula (VII) having a cytotoxic substance linked thereto is made to react with an immunoglobulin or its fragment expressed by formula (VI) having an active disulfide group.

In the abovementioned methods, it is desirable to use 0.3 to 20 moles of a serum albumin expressed by formula (V) having an active disulfide group and having a cytotoxic substance linked thereto to 1 mole of an immunoglobulin or its fragment expressed by formula (IV) having a thiol group. The reaction can be carried out by mixing both proteins in a buffer solution adjusted to pH 6 to 10 in such a way as to have the total protein concentration of 0.5 to 100 mg/ml (more desirably 1 to 20 mg/ml), followed either by allowing the reaction to stand at 0° to 60° C., or by dialyzing the reaction mixture against a buffer having the same pH as the reaction mixture. The reaction time varies depending upon the reaction scale and conditions; however, it usually ranges between 4 hours and 3 days. The separation of the obtained conjugate having cytotoxicity from the reaction mixture and its purification can be effected according to the ordinary procedures, for instance, by means of dialysis and gel filtration chromatography.

(2) A method in which an immunoglobulin or its fragment expressed by formula (IV) having a thiol group and a serum albumin expressed by formula (VII) having a cytotoxic substance linked thereto are found to each other by use of a cross-linking agent of formula (IX) which is able to react with the thiol groups of both proteins.

In the above method, the reaction can be carried out by simultaneously bringing an immunoglobulin or its fragment having a thiol group, a cross-linking agent, and a serum albumin having a cytotoxic substance linked thereto into direct contact with each other; however, it is desirable to carry on the process first by making one of the proteins react with a cross-linking agent and then by allowing the reaction product to react with the other of the proteins. In this latter case, 0.8 to 50 moles of a cross-linking agent and 0.8 to 10 moles of the other of the proteins are used to 1 mole of the protein which is to react with the cross-linking agent at first. The reaction is initiated by adding a cross-linking agent, which is dissolved in a small quantity of such a solvent as N,N'-dimethylformamide, dimethyl sulfoxide, 1,2-dimethoxyethane, methanol, ethanol, acetone, etc., to a buffer solution with the pH adjusted to 6 to 10 containing an immunoglobulin or its fragment having a thiol group or a serum albumin having a cytotoxic substance linked thereto (the solution is to be prepared to have the protein concentration of 0.5 to 100 L mg/ml preferably, and 1 to 20 mg/ml more preferably) at a temperature ranging from 0° to 60° C. with stirring. After the removal of the cross-linking agent which remained unreacted by means of dialysis or gel filtration chromatography, a buffer solution of pH 6 to 10 containing the other of the proteins (the preferable range of protein concentration is the same as that mentioned above) is added to it and the reaction is carried out at 0° to 60° C. The separation and purification of thus obtained conjugate having cytotoxicity from the reaction mixture can be effected according to ordinary methods such as gel filtration chromatography.

(3) A method in which a serum albumin expressed by formula (VII) having a cytotoxic substance linked thereto and an immunoglobulin or its fragment expressed by formula (VIII) having introduced maleimide group(s) are made to react with each other.

In this method, it is desirable to use 0.3 to 10 moles of a serum albumin expressed by formula (VII) having a cytotoxic substance linked thereto to 1 mole of an immunoglobulin or its fragment expressed by formula (VIII) having introduced maleimide group(s). The reaction can be carried out by mixing these two protein in a buffer solution with its pH adjusted to 6 to 10 in such a way as to obtain the total protein concentration of 0.5 to 100 mg/ml (more preferably 1 to 20 mg/ml) and then by allowing the reaction mixture to stand at 0° to 60° C. The time required for completing the reaction varies depending upon the reaction scale and conditions but it generally ranges from 4 hours to 3 days. The obtained conjugate having cytotoxicity is separated from the reaction mixture and purified according to the ordinary method such as dialysis and gel filtration column chromatography.

The present invention is described in detail by the following examples and a referential example.

REFERENTIAL EXAMPLE 1

(a) Preparation of anti mouse leukemia L1210 IgG

An emulsion prepared from $1 \times 10^6$ mouse leukemia L 1210 cells and Freund's complete adjuvant was intravenously injected into a rabbit. Thereafter, $1 \times 10^6$ L 1210 cells, together with the adjuvant, were further subcutaneously injected three times at intervals of one week, and the rabbit eight days after the day of final injection. The portions of blood thus obtained were pooled and mixed, and the serum was separated therefrom and heated at 56° C. for 30 minutes for inactivation. Two hundred ml of saturated aqueous solution of ammonium sulfate was added to 200 ml of thus obtained anti-L 1210 antiserum and the resulting precipitate was separated by means of centrigugation. The precipitate thus separated was dissolved in 50 ml of 0.01M phosphate buffer (pH 7.6) and was further dialyzed thoroughly against the same buffer. The dialyzate was subjected to DEAE cellulose column chromatography (column size 3 cm × 94 cm) equilibrated with the same buffer to obtain a solution containing anti-L 1210 IgG as an unadsorbed fraction.

(b) Separation of fragment F(ab')$_2$ from immunoglobulin.

One point two g of anti-L 1210 IgG obtained in the preceding (a) was dissolved in 40 ml of 0.1M acetate buffer (pH 4.5), to which 24 mg of pepsin was added to effect peptic digestion at 37° C. for about 18 hours. The digestion product was subjected to Sephadex G200 column chromatography (column size 3.5 cm×140 cm) over saline to take out a protein eluted at molecular weight of about 100,000 as a pure fragment F(ab')$_2$.

(c) Preparation of fragment Fab'

Twenty μl of an aqueous solution of 150 mM 2-mercaptoethanol was added to 2.0 ml of 0.01M tris-hydrochloride—0.14M sodium chloride (hereinafter referred to as NaCl)—2 mM ethylenediaminetetraacetic acid (hereinafter referred to as EDTA) solution (pH 8.3) containing 18.4 mg of fragment F(ab')$_2$ obtained in the preceding (b) and the mixture was subjected to the reduction reaction at 37° C. for 1 hour. After the reaction was over, the solution was put to Sephadex G25 column chromatography (column size 1.0 cm×20 cm) equilibrated with 5 mM acetate buffer—0.14M sodium chloride—1 mM EDTA solution (pH 5.5) (hereinafter referred to as ANE buffer) to remove 2-mercaptoethanol, thus giving fragment Fab' having 1 thiol group.

(d) Purification of IgM

One hundred ml of saturated aqueous solution of ammonium sulfate was added to 100 ml of anti-L 1210 antiserum obtained according to the aforesaid (a) and the resulting precipitate was separated by centrifugation. The obtained precipitate was dissolved in a small quantity of 0.9% potassium chloride solution. After the caused insoluble substance was removed by centrifugation, the solution was put to Sephadex G-200 column chromatography (column size 2.2 cm×102 cm) equilibrated with 0.9% sodium chloride solution to obtain a fraction of IgM at the first peak. A saturated aqueous solution of ammonium sulfate was added to the obtained fraction of IgM, both being equal to each other in volume. After the resulting precipitate was separated by centrifugation, it was dissolved in a small amount of 0.9 sodium chloride solution and dialyzed thoroughly against 0.9 sodium chloride solution.

(e) Preparation of IgMs 1.8 ml of rabbit IgM dissolved in 0.9% sodium chloride (9.5 mg/ml) and 0.2 ml of 0.2M cysteine dissolved in 1M tris.hydrochloride buffer (pH 8.6) were mixed together. After the mixture was reduced at room temperature for 16 hours, excess systeine was removed by gel filtration (5 mM acetate buffer—0.14M NaCl—1 mM EDTA (pH 5.5)) with the use of Sephadex G-25 (column size 0.8 cm×43 cm).

(f) Preparation of anti mouse breast cancer MM 46 monoclone antibody

Anti MM 46 IgG2b antibody producible hybridomas obtained by the cell hybridization method (Seto et al., Journal of Immunology, Vol. 128, pp. 201~205, 1982) were intraperitoneally inoculated to fifteen nude mice, $2 \times 10^7$ hybridomas cells for each mouse, and their ascites were collected ten days after the inoculation. 50 ml of the obtained ascites was dialyzed thoroughly against 5 l of 0.1M phosphate buffer (pH 8.0). The dialyzate was then subjected to protein A Sepharose column (column size 1.5 cm×12.5 cm) sufficiently equilibrated with the same buffer to let the unadsorbed proteins flow out adequately. After that, impure proteins were eluted with 0.1M citric acid buffer (pH 5.0) and then adsorbed IgG2b was eluted with 0.1M citric acid buffer (pH 3.0). The eluate had its pH adjusted back to neutral with the use of 2M Tris-HCl buffer (pH 8.2) and then dialyzed against 5 l of 20 mM phosphate buffer (pH 7.5) sufficiently to give 105 mg (17.7 ml) of anti MM 46 monoclone antibody (IgG2b). Also, 25 mg (7.0 ml) of nonimmunized IgG2b was obtained from 50 ml of normal mouse serum according to the same procedure as that mentioned above.

EXAMPLE 1

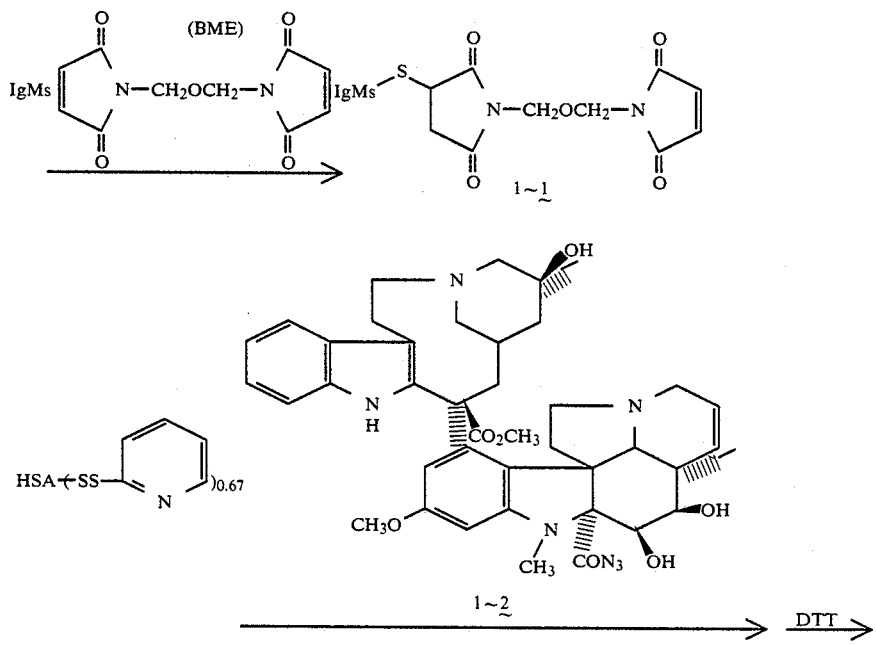

-continued (VBL)

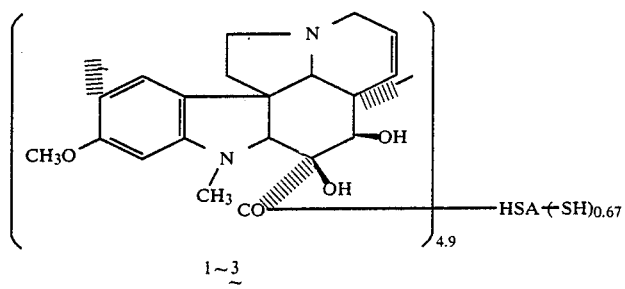

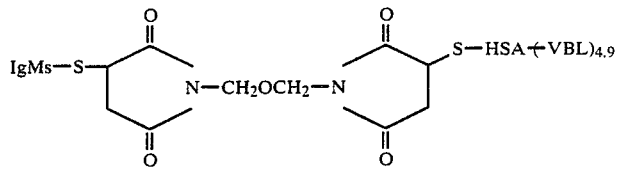

1-(a)

One point eight ml of a buffer (5 mM acetate buffer—0.14M sodium chloride, pH 5.5, hereinafter referred to as buffer A) containing 12.4 mg of IgMs obtained in Referential example 1, (e), dissolved therein and 1.8 ml of saturated solution of cross linking agent N,N'-bis(maleimidemethyl)ether (hereinafter referred to as BME) dissolved in a buffer A were mixed and allowed to react with each other at room temperature for 30 minutes. Thereafter, the excess BME was removed by gel filtration by means of Sephadex G-25 (column size 0.8 cm×43 cm, buffer A used as solvent). The fractions were collected and 7.7 ml of a solution containing 10.2 mg of modified IgMs was obtained (1∼1). This solution was succeedingly used in the reaction of 1-(c).

1-(b)

A desacetylvinblastic acid azide intermediate expressed by formula 1∼2 was obtained according to the generally known method (C. J. Barnett, Journal of Medicinal Chemistry, Vol. 21, pp. 88∼96, 1978). More particularly, 10 mg of desacetylvinblastic acid hydrazide was dissolved in 0.5 ml of 1N hydrochloric acid and 0.15 ml of 0.1N sodium nitrite solution was added to the solution at 0° C. After the reaction was continued for 5 minutes, 0.5 ml of tetrahydrofuran was added to the reaction mixture, which was then neutralized with 0.5 ml of 1N sodium hydroxide to obtain a solution containing a reactive desacetylvinblastic acid azide intermediate expressed by formula 1∼2. Then 5.0 ml of 0.2M boric acid buffer (pH 9.0) containing 46 mg of 2-thiopyridylated human serum albumin (HSA) obtained in Example 3, 3-(a), described later, was added to the above solution and the mixture was stirred at room temperature for 2 hours. Also, 0.1 ml of 1N ammonia was added to the mixture and the reaction was continued for another 2 hours. The reaction mixture was passed through a column (1 cm×40 cm, 0.1M phosphate—0.1M sodium chloride buffer used as solvent, pH 7.5) of Sephadex G-25 and desired fractions were collected (12.5 ml) to exchange the solvents.

Then 4.0 μl of 1M dithiothreitol (DTT) (0.1M phosphate buffer used as solvent, pH 7.5) was added to the pooled fraction at 4° C. and the reaction was carried on for 1.5 hours (1∼3). The reaction mixture was put in a cellophane tube and dialyzed thoroughly against the buffer A at 4° C. The concentrations of the protein and the drug of the reaction product contained in the recovered solution (13.0 ml) were determined by measuring the absorbances at 280 nm and 270 nm, and then relating the obtained values to the respective absorbances of unmodified human serum albumin and unmodified vinblastin obtained at the same wave lengths. The quantity of human serum albumin protein was 35 mg and that one molecule of the human serum albumin had an average of 4.9 molecules of the drug linked thereto calculated from the quantitative ratio between the desacetylvinblastin residue (VBL) and the protein. The number of thiol groups of the human serum globulin was 0.67 in average when determined according to the method described in Example 2, 2-(c).

1-(c)

2.0 ml of a solution of modified IgMs obtained in 1-(a) and 3.0 ml of a solution of human serum albumin linked with desacetylvinblastin obtained in 1-(b) were mixed and made to react with each other at 4° C. overnight. When the reaction mixture was examined by sodium dodecyl sulfate electrophoresis, it was confirmed that the reaction product contained a hybrid expressed by formula 1∼4 comprising IgMs and HSA linked together. The reaction product was purified by gel filtration with the column (column size 1.5 cm×90 cm) of Sephadex G-150 super fine to obtain the desired hybrid.

EXAMPLE 2

IgG: L 1210 rabbit IgG

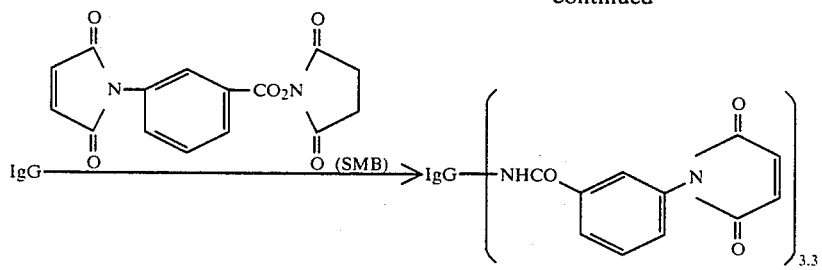

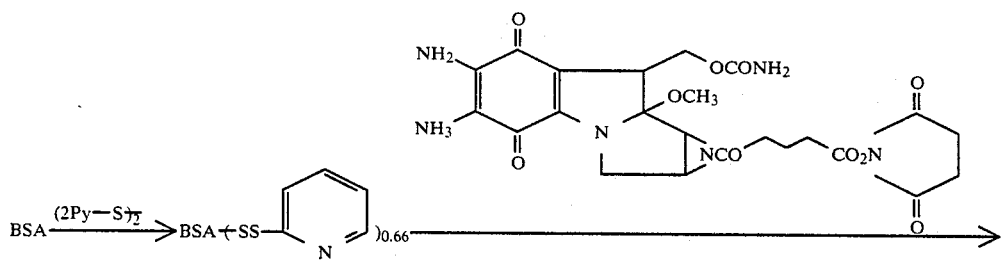

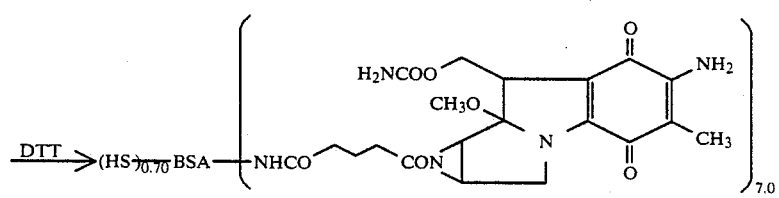

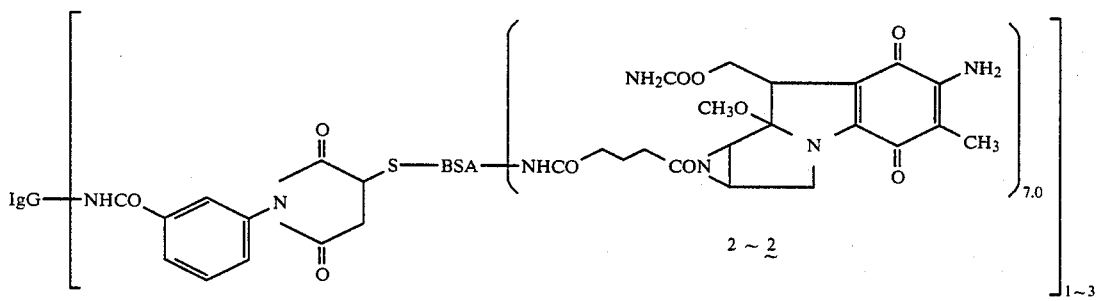

2-(a) Preparation of IgG antibody having introduced maleimide group 30 mg of rabbit IgG obtained in the aforementioned Referential Example 1, 1-(a), was dissolved in 0.1M phosphate buffer—0.1M sodium chloride (hereinafter referred to as NaCl) (pH 7.0) to make 1.0 ml of a solution, to which 20 μl of 100 mM dimethylformamide (hereinafter referred to as DMF) solution of N-succinimidyl m-maleimidobenzoate (hereinafter referred to as SMB) was added at room temperature. After the reaction mixture was stirred moderately for 35 minutes, it was immediately passed through a column (1.0 cm×40 cm, 0.1M phosphate buffer, pH 6.5) of Sephadex G-25 to remove low molecules, thus obtaining 9.5 ml of solution which contained rabbit IgG having a maleimide group introduced (2~1).

The quantity of IgG contained in the obtained solution was confirmed to be 29.2 mg from the absorbance determined at 280 nm.

The number of maleimide groups introduced to the molecules of IgG was determined as follows. 5 μl of 100 mM DMF solution of N-(2,4-dinitropheny)cysteine (hereinafter referred to as DNP cysteine) was added to 1.0 ml of the obtained solution and the reaction mixture was left standing overnight at 4° C. The reaction solution was passed through Sephadex G-25 (0.01M sodium phosphate buffer—0.14M NaCl, pH 7.0) with 0.01M sodium phosphate buffer—0.14M NaCl and the protein eluates were pooled. The concentration of IgG was determined from the absorption maxima at 280 nm and the concentration of the DNP-cysteine residue reacted with the maleimide group was determined from the absorption maximum at 360 nm. The calculational value of the concentration of IgG was corrected on the basis that the absorbance of DNP-cysteine at 280 nm was 28.1% of the maximum value obtained at 360 nm.

The number of the maleimide groups, which were reactive with DNP-cysteine, introduced into the molecules of IgG was determined following the abovementioned procedure.

$$\frac{(DNP)}{(IgG)} = \frac{\text{Absorbance of DNP}}{\text{Molecular extinction coefficient of DNP}} \bigg/$$

$$\frac{\text{Absorbance of IgG}}{\text{Molecular extinction coefficient of IgG}} = \frac{0.237}{17,000} \bigg/$$

$$\frac{0.802}{2.025 \times 10^5} = 3.52$$

Also, the following experiment was performed to rectify errors in the measurements which were attributable to the nonspecific adsorption of DNP-cysteine, which was used in the determination of the number of maleimide groups, by IgG.

5.0 μl of the aforementioned DNP-cysteine solution was added to 1.0 ml of 0.1M phosphate buffer—0.14M Nacl (pH 6.5) containing 3.15 mg of rabbit IgG. After the mixture was left standing overnight at 4° C., its separation was carried out with the use of Sephadex G-25 according to the same way as the above and the protein eluates were pooled.

The number of DNP-cysteine adsorbed by one molecule of IgG was obtained from the adsorbances determined at 280 nm and 360 nm as follows:

$$\frac{(DNP)}{(IgG)} = \frac{0.008}{17,000} \bigg/ \frac{0.504}{2.025 \times 10^5} = 0.19$$

When the number of maleimide groups obtained in the above is rectified with this value, the result is $3.52 - 0.19 = 3.33$. The rectified number of maleimide groups introduced into a molecule of IgG is 3.33.

2-(b) Preparation of bovine serum albumin containing 2-pyridyldithio group 132 mg of bovine serum albumin (hereinafter referred to as BSA) in the crystal form (commercially available) was dissolved in 5.0 ml of 0.1M sodium phosphate buffer—0.1M NaCl—1 mM EDTA solution (pH 7.0) and a solution prepared by dissolving 4.4 mg of 2-pyridyldisulfide in 0.1 ml DMF was added thereto. The mixture was allowed to react overnight at 4° C. The reaction solution was placed in a cellophane tube and was dialyzed against 0.01M phosphate buffer—0.4M NaCl—1 mM EDTA (ph 7.0) at 4° C. for 2 days. The recovered dialyzate was passed through a column (1 cm×40 cm) of Sephadex G-25 (0.01M phosphate buffer—0.14M NaCl—1 mM EDTA, pH 7.0) to obtain 10.2 ml of the protein eluates. The quantity of the recovered BSA was 96.3 mg (based on the absorbance at 280 nm).

The number of active disulfide residue of the obtained BSA having 2-pyridyldithio group was quantified on the basis of the absorbance determined from the absorption maximum value (at 343 nm) of the thiopyridone which was released by excess dithiothreitol made to react on part of the sample. While, the quantity of BSA contained in the sample was obtained by determining the absorbance at 280 nm. The number of active disulfide group existing in one molecule of BSA is expressed by the ratio of these measurements. It may be expressed by the concentration ratio as follows:

$$\frac{(2\text{-pyridylthio group})}{(BSA)} = \frac{0.089}{8080} \bigg/ \frac{0.725}{43600} = 0.66$$

2-(c) Preparation of BSA (2∼2) linked to mitomycin C (hereinafter referred to as MMC)

A solution prepared by dissolving 4.11 mg of 1a-(4-(N-succinimidoxycarbonyl)butyryl)mitomycin C (MMC derivative) in 50 μl of DMF was added to 1.5 ml of 0.03M phosphate buffer—0.03M NaCl containing 14.1 mg of BSA having 2-pyridyldithio group, which was obtained in the preceding 2-(b), dissolved therein. After the mixture was stirred at 4° C. for 5 hours, 4.28 μl of 1M dithiothreitol solution of the same buffer was added thereto and was kept at 4° C. for 1.5 hour. The reaction solution was dialyzed against 0.01M acetate buffer—0.14M NaCl—0.01 mM EDTA (pH 5.25) at 4° C. for 17 hours. The quantity of BSA having MMC linked thereto contained in 1.60 ml of the recovered dialyzate was determined to be 14 mg based on the absorbance at 280 nm.

Also, the following determinations were made as to BSA (2∼2) having MMC linked thereto contained in the recovered dialyzate by use of part of the recovered dialyzate.

Determination of MMC linked to a BSA molecule (MMC/BSA)

The quantity of MMC residue was determined from the absorbance at 360 nm where MMC showed the absorption maximum and the quantity of BSA was also determined from the absorbance at 280 nm where BSA showed the absorption maximum. However, the absorbance of BSA was rectified on the basis that the absorbance of MMC at 280 nm is 4.1% of the absorption maximum at 360 nm. The result is $$(\text{MMC residue})/(\text{BAS}) = \frac{959 \, \mu M}{137 \, \mu M} = 7.0$$

Determination of thiol group regenerated in BSA molecule (HS-/BSA)

Part of the reaction product was dissolved in a solution of 0.1M phosphate buffer—0.1M NaCl—1 mM EDTA (pH 7.6) and excess 5,5'-dithiobis-(2-nitrobenzoic acid) (DTNB) was added thereto. The mixture was allowed to react overnight at 4° C. The reaction solution was passed through a column of Sephadex G-25 (0.01M-sodium phosphate buffer—1.14M NaCl—1 mM EDTA) and the protein eluates were pooled. The concentration of BSA contained in the pooled eluate was determined from the absorbance at 280 nm and furthermore the concentration of the thiol group contained in BSA linked with MMC was determined from the absorbance at 412 nm resulting from the 5-mercapto-2-nitrobenzoic acid which was released by added excess dithiothreitol. The value of the ratio between them was calculated as follows:

(Thiol residue)/(BSA)=(1.47)/(2.10)=0.70

From the above-mentioned determination, the obtained albumin linked to MMC can be expressed by formula 2∼2 as follows:

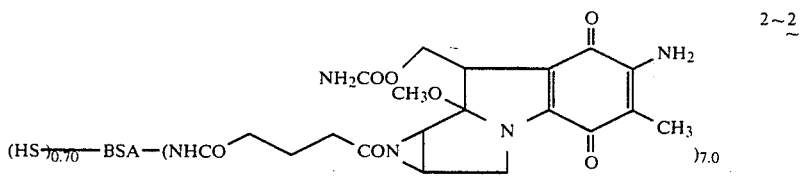

2-(d) Preparation of conjugate (2~3) by reaction of SMB-treated IgG with MMC-linked BSA 1.5 ml of solution (0.1M phosphate buffer—0.1M NaCl, pH 6.5) of IgG containing an average of 3.33 maleimide groups obtained in the aforementioned 2-(a) was mixed with 1.5 ml of solution (0.01M acetate buffer—0.14M NaCl—0.01 mM EDTA, pH 5.25) of BSA linked with an average of 7.0 MMC's obtained in the preceding 2-(c) and the mixture was allowed to react overnight at 4° C. Upon examination of the reaction solution by sodium dodecylsulfate (hereinafter referred to as SDS) electrophoresis, it was confirmed that the obtained product was mainly composed of the conjugate (2~3) comprising IgG bound with 1 to 3 MMC-linked BSA's. The hybrid was purified on a column (1.8 cm × 80 cm) of Sephadex G-150 super fine.

2-(e) Cytotoxicity of the conjugate (2~3) against L 1210 cells

The cytotoxicity of the conjugate (2~3) obtained in the preceding 2-(d) against the target L 1210 cells was examined.

0.9 ml of Roswell Park Memorial Institute 1640 (hereinafter referred to as RPMI 1640) culture medium (containing 10% calf serum, 20 μM 2-mercaptoethanol and 0.1 mg/ml of kanamycin) containing $5 \times 10^4$ of L 1210 cells was placed in the wells of a 24-hole culture plate, to which 0.1 ml of subject samples diluted to varied concentrations were added. The culture was carried out at 37° C. in an atmosphere of 5% $CO_2$ for 48 hours and then the viable cell number was determined by trypan blue dye exclusion. Result: as shown in Table 1, the conjugate (2~3) displayed a remarkable effect of prohibiting the proliferation against the target L 1210 cells with a clear dependency. The culture was carried out in two groups and the values shown are their averages.

TABLE 1

| Corresponding concentration of mitomycin of conjugate (2~3) (μM) | Number of viable cells after 48 hours of culture ( × $10^{-4}$/ml) |
|---|---|
| 0 | 45 |
| 0.1 | 45 |
| 1.0 | 37 |
| 10 | 8.3 |

EXAMPLE 3

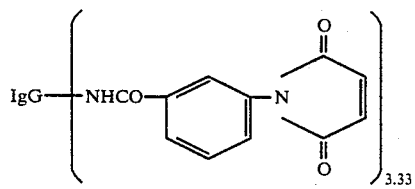

3~1 (Prepaired in Example 2, 2 - (a))

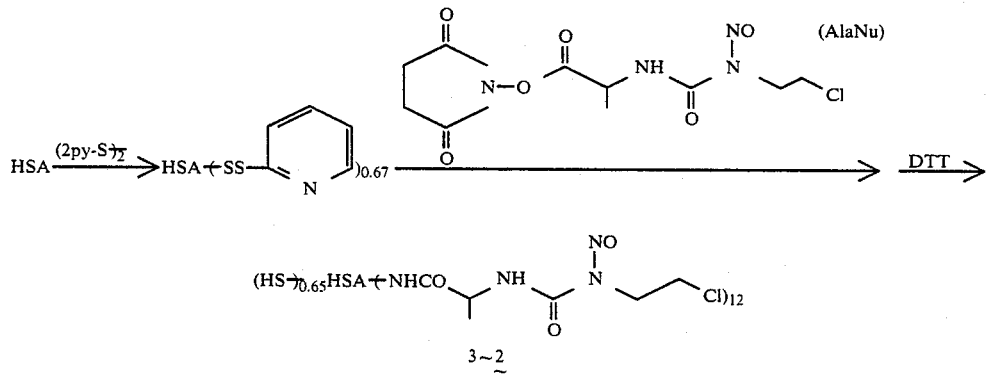

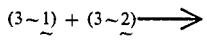

(3~1) + (3~2) ⟶

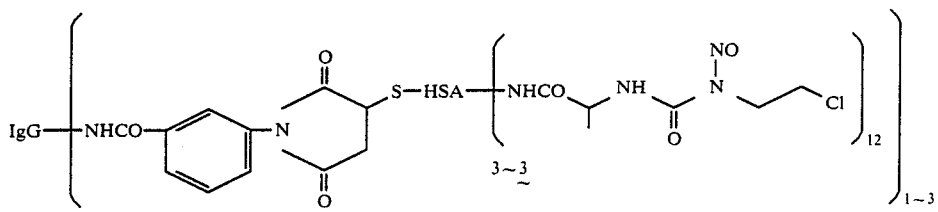

3-(a) Preparation of human serum albumin having 2-pyridyldithio group 132.0 mg of lyophilized human serum albumin (HSA) was dissolved in 5.0 ml of 0.1M phosphate buffer—0.1M NaCl—1 mM EDTA (pH 7.0), to which a solution prepared by dissolving 4.0 mg of 2-pyridyldisulfide in 0.1 ml of DMF was added. The mixture was then allowed to react overnight at 4° C. The reaction solution was passed through a column (1 cm×40 cm) of Sephadex G-25 (0.01M phosphate buffer—0.14M NaCl—1 mM EDTA, pH 7.0) to obtain 8.7 ml of protein eluate. The recovered HSA was 122 mg (based on the absorbance at 280 nm).

The quantity of active disulfide residue on HSA treated with 2-pyridyldisulfide was determined in the same way as BSA treated with 2-pyridyldithio of Example 2, 2-(a). The result was $$\frac{\text{(2-pyridyldithio group)}}{\text{(HSA)}} = 0.67$$

3-(b) Preparation of HSA carrying nitrosourea groups (3~2)

20 μl of dimethylformamide solution containing 1.0 mg of N-succinimidyl 2-((3-chloroethyl)-3-nitrosoureido) propionate (AlaNu) dissolved therein was added at 4° C. to 20 ml of 0.1M dosium phosphate—0.1M NaCl (pH 7.5) buffer containing 13.2 mg of HSA—SS-2py)$_{0.67}$, which has an average of 0.67 2-pyridylsulfide group per one molecule of HSA, dissolved therein and the mixed solution was left to react at the same temperature for 8 hours. Then 4.0 μl of 1M dithiothreitol dissolved in the same buffer solution was added to the reaction mixture and was allowed to react at 4° C. for 1.5 hour. The reaction solution was then put in a cellophane tube and was dialyzed thoroughly at 4° C. against 0.9% saline—1 mM EDTA to remove low molecular substances therefrom, thus obtaining 3.1 ml of a recovered solution containing HSA (3~2) having nitrosourea groups linked thereto.

Based upon the determination of the absorbance at 280 nm, it was confirmed that the obtained solution contained 11.7 mg of HSA and that the modified HSA thus obtained had an alkylating function per 1 mole of HSA equal to that of 12 moles of N-succinimidyl 2-((3-chloroethyl)-3-nitrosoureid) propionate when examined according to the method of measuring alkylation function (G. P. wheeler et al., Cancer Research, Vol. 34, pp. 194~200, 1974).

It was also made clear that one moleculer of HSA had an average of 0.65 thiol, when the number of thiol regenerated on the molecule of HSA was determined according to the same method as Example 1, 1-(c).

Accordingly, the obtained HSA (3~2) having nitrosourea group linked thereto is expressed as follows:

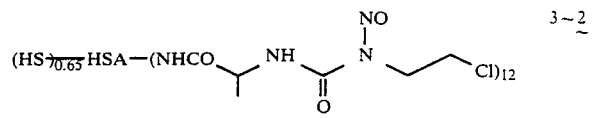

3-(c) Preparation of conjugate (3~3) by reaction between IgG having introduced maleimide group and HSA having nitrosourea group linked thereto 1.0 ml of 0.1M phosphate buffer—0.1M NaCl (pH 6.5) solution of IgG having an average of 3.33 maleimide group introduced thereinto obtained in Example 2, 2-(a), and 1.8 ml of a solution (0.9% saline) of HSA (3~2) having an average of 12 nitrosourea groups obtained in the preceding 3-(b) were mixed and allowed to react overnight at 4° C. Upon examination of the reaction solution by SDS electrophoresis, it was confirmed that the reaction product was mainly composed of the conjugate comprising IgG having 1 to 3 linked HSA which carry nitrosourea group expressed by formula 3~3.

The hybrid was purified with a column (1.5 cm×80 cm) of Sephadex G-150 super fine.

3-(d) Cytotoxicity of hybrid (3~3) against L 1210 cells

The hybrid (3~3) obtained according to the preceding 3-(c) was examined as to its cytotoxicity against the target L 1210 cells as follows.

0.9 ml of RPMI 1640 culture medium (containing 10% calf serum, 20 μM 2-mercaptoethanol and 0.1 mg/ml of kanamycin) containing 5×10$^4$/ml of L 1210 cells was placed in wells of a 24-hole culture plate, to which 0.1 ml of subject samples diluted to varied concentrations were added. The culture was carried out at 37° C. in an atmosphere of 5% CO$_2$ for 48 hours and then the viable cells were counted by dye exclusion with Trypan Blue.

Table 2 shows the result indicating that the conjugate (3~3) had a remarkable effect of prohibiting the proliferation of the target L 1210 cells depending to the concentrations. The culture was carried out in two groups and the values show their averages.

TABLE 2

| Corresponding concentration of nitrosourea of hybrid (3~3) (μM) | Number of viable cells after 48 hours of culture (×10$^{-4}$/ml) |
|---|---|
| 0 | 34 |
| 0.1 | 35 |
| 1.0 | 28 |
| 10 | 5.1 |

EXAMPLE 4

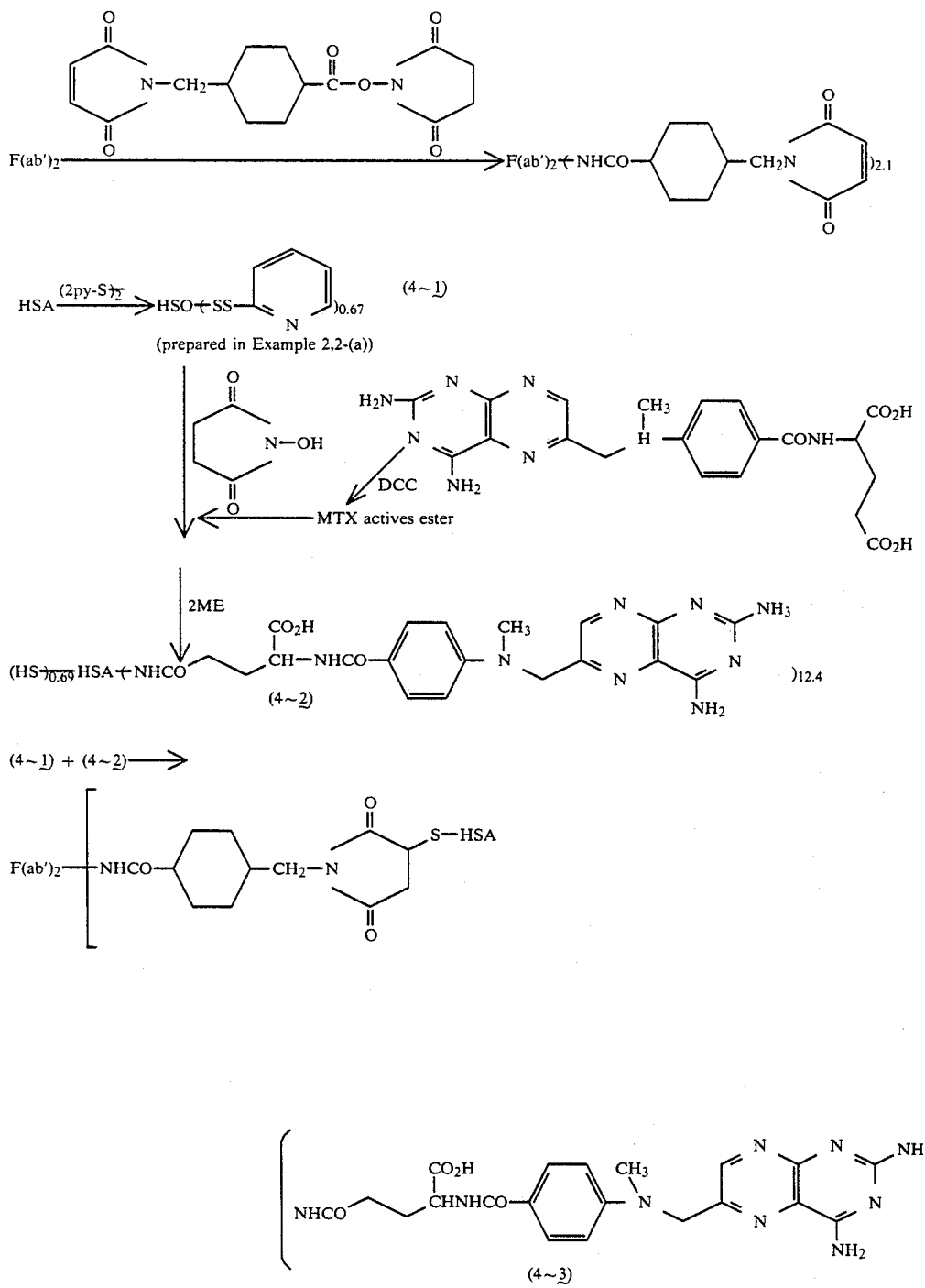

4-(a) Preparation of F(ab')$_2$ having maleimide group introduced thereinto 1.0 ml of 0.1M phosphate buffer—0.1M NaCl (pH 7.0) solution containing 20 mg of rabbit F(ab')$_2$ obtained in the aforementioned Referential Example 1, 1-(b), was prepared, and 10 μl of 100 mM DMF solution of 4-(maleimidemethyl)cyclohexane-1-carboxylic acid N-hydroxysuccinimide ester (hereinafter referred to as MCAE, see K. Kato, Y. Hamaguchi, E. Ishikawa, Chemistry and Organism, Vol. 14, p. 817, 1976) was added to the previously prepared solution at room temperature and stirred slowly for 30 minutes. The reaction solution was then passed through a column of Sephadex G-25 (1.0 cm×30 cm, 0.1M phsophate buffer—0.1M NaCl, pH 6.5) to remove the low molecular substance, thus obtaining 7.6 ml of a solution containing rabbit F(ab')$_2$ reacted with MCAE.

The quantity of protein of F(ab')$_2$ (4~1) containing maleimide group contained in the obtained solution was 17.0 mg when determined from the absorbance at 280 nm. The number of maleimide groups introduced into a molecule of F(ab')$_2$ was 2.1 in average when determined according to the same procedures taken for the determination of maleimide groups introduced into IgG in the case of Example 2, 2-(a).

4-(b) Preparation of HSA (4~2) carrying methotrexate (MTX)

100 μl of DMF solution containing 3.3 mg of N-hydroxysuccinimide ester of MTX prepared according to the publicly known method (P. N. Kulkarni et al., Cancer Research, Vol. 41, pp 2700~2706) was added to 2.0 ml of 0.1M sodium phosphate—0.1M NaCl (pH 7.5) solution containing 13.2 mg of HSA having an average of 0.67 2-pyridyldithio group obtained in Example 4, 4-(a), at 4° C. and the reaction was made to continue for 10 hours. Then 5.0 μl of 1M 2-mercaptoethanol dissolved in the same buffer and the reaction was continued at 4° C. for another 1.5 hour. The reaction solution was put in a cellophane tube and dialyzed thoroughly against 0.9% saline—1 mM EDTA at 4° C. to remove the low molecular substances, thus obtaining 3.40 ml of a solution containing HSA (4~2) having MTX bound thereto.

The concentrations of protein and MTX contained in the recovered solution were calculated from the respective absorptions obtained at 280 nm and 307 nm and then determined in correlation with the absorbances of the unmodified HSA and unmodified MTX at the same two wave lengths.

The number of thiol groups regenerated in the molecules of HSA was then determined after the same DTNB method that was adopted in Example 2, 2-(c). Result: the quantity of protein obtained from the recovered solution was 9.8 mg, the MTX bonded to HSA molecules was 12.4 molecules, and the number of thiol groups regenerated in HSA was 0.69. Therefore, the obtained HSA having MTX residues linked thereto is expressed by formula 4~2 as follows:

3~2 obtained in Example 3, 3-(b) were mixed at 4° C. and made to react overnight.

It was confirmed by subjecting the reaction solution to SDS electrophoresis that the reaction product was mainly composed of the conjugate, expressed by formula 4~3, having 1 to 3 HSA linked to MTX. The purification of the conjugate was carried out by passing the reaction solution through a column (1.5 cm × 80 cm) of Sephadex G-150 super fine.

4-(d) Cytotoxicity of the conjugate (4~3) against L 1210 cells 0.9 ml of RPMI 1640 culture medium (containing 10% calf serum, 20 μM 2-mercaptoethanol and 0.1 mg/ml of kanamycin) with $5 \times 10^4$/ml of L 1210 cells contained therein was put in the wells of a 24-hole culture plate, to which 0.1 ml of subject samples diluted to varied concentrations were added. The culture was made at 37° C. in an atmosphere of 5% $CO_2$ for 48 hours and the viable cells were counted by dye exclusion with Trypan Blue.

The result is given in Table 3, from which it is proved that the conjugate (4~3) has a remarkable effect of prohibiting the proliferation against the target L 1210 cells corresponding to the concentrations. The culture was made in two groups and the values are their averages.

TABLE 3

| Corresponding concentration of methotrexate of hybrid (4~4) (μM) | Number of viable cells after 48 hours of culture ( × $10^{-4}$/ml) |
|---|---|
| 0 | 51 |
| 0.1 | 49 |
| 1.0 | 29 |
| 10 | 8.4 |

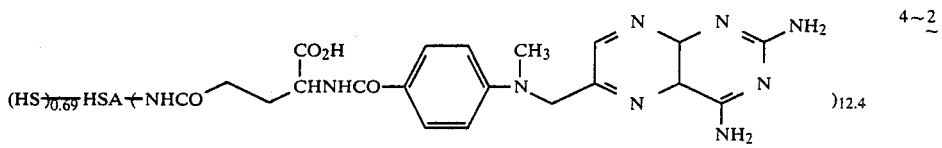

4-(c) Preparation of conjugate (4~3) by reaction between F(ab′)$_2$ containing maleimide group and HSA having MTX linked thereto.

1.0 ml of 0.1M sodium phosphate buffer—0.1M NaCl (pH 6.5) solution of F(ab′)$_2$ having an average of 2.1 introduced maleimide groups expressed by formula 4~1 obtained in Example 4, 4-(a), and 2.0 ml of 0.9% NaCl—1 mM EDTA solution containing HSA having an average of 12.4 MTX residues expressed by formula

EXAMPLE 5

An antitumor conjugate, in which fragment F(ab′)$_2$ and HSA having MTX linked thereto were bound each other with their respective amino groups and thiol groups through the cross linking agent SMB, was prepared according to the same method as Example 3, except that SMB was used in place of MCAE which was used in Example 4.

EXAMPLE 6

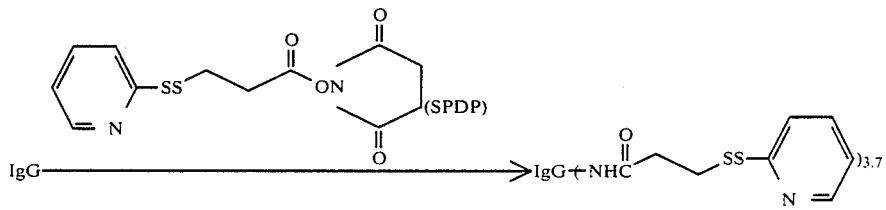

-continued

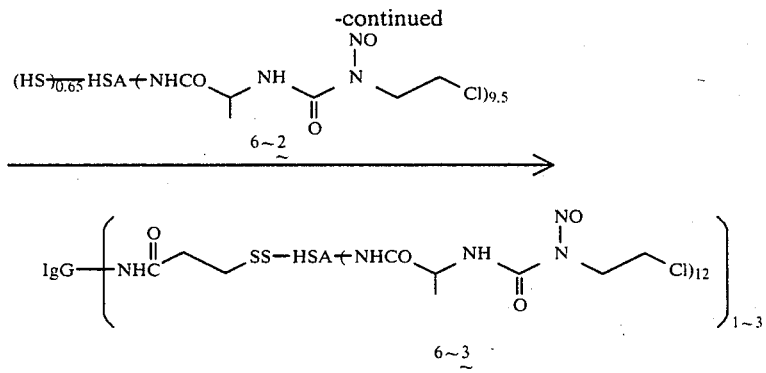

6-(a) Introduction of active disulfide group into IgG (preparation of 6~1)

8.0 μl of 100 mM DMF solution of N-succinimidyl-3-(2-pyridylthio)propionate (SPDP) was added to a solution prepared by dissolving 20 mg of mouse monoclone IgG2b antibody, which was obtained in the aforementioned Referential Example 1, 1-(f), in 1.0 ml of 0.1M phosphate buffer—0.1M NaCl (pH 7.5) at room temperature and the mixture was stirred slowly for 30 minutes. Then the reaction solution was passed through a column (1.0 cm×30 cm) of Sephadex G-25 (0.1M phosphate buffer—0.1M NaCl, pH 6.5) to remove the low molecular weight substance, thus obtaining 7.5 ml of solution of mouse IgG having an active disulfide group introduced thereinto (6~1).

The quantity of IgG contained in the solution thus obtained was 18 mg when determined from the absorbance at 280 nm. The number of the active disulfide groups introduced into IgG was determined following the procedure mentioned below.

A small portion of the abovementioned solution was diluted with the same buffer and then its absorbance at 280 nm was obtained to determine the molar concentration of IgG. Next, excess 2-mercaptoethanol was added to the solution, and after the mixture was left standing still for 1 minute, the absorbance at 343 nm resulting from the liberated 2-mercaptopyridine was determined to obtain the concentration of the active disulfide group. It was confirmed from the ratio of these values that IgG had an average of 3.7 2-pyridyldithio groups introduced.

6-(b) Preparation of conjugate (6~3) by reaction between IgG2b having active disulfide and HSA linked with AlaNU (6~2)

0.5 ml of a solution of IgG containing 3.7 2-pyridyldithio groups in average obtained in the preceding 6-(a) and 1.5 ml of a solution (0.9% NaCl—1 mM EDTA solution) containing 5.3 mg of human serum albumin linked with nitrosourea group expressed by formula 6~2 prepared according to the same method as Example 3, 3-(b), were mixed together and allowed to react overnight at 4° C. When the reaction solution was examined by SDS electrophoresis, it was ascertained that the reaction product was mainly composed of conjugate with 1 to 3 HSA's containing nitrosourea groups expressed by formula 6~3. The conjugate was purified with the use of a column (1.5 cm×80 cm) of Sephadex G-150 super fine.

6-(c) Cytotoxicity of conjugate (6~3) against MM46 cells

The cytotoxicity of the conjugate (6~3), which was prepared according to the preceding 6-(b), against the target MM46 cells was examined.

0.2 ml of RPMI 1640 culture medium (containing 10% calf serum, 20 μM 2-mercaptoethanol and 0.1 mg/ml of kanamycin) containing $5 \times 10^3$/ml of MM46 cells was placed in wells of a 96-hole culture plate, to which 20 μl of subject samples diluted to varied concentrations were added. The culture was carried out at 37° C. in an atmosphere of 5% $CO_2$ for 48 hours and the viable cells were counted by trypan blue dye exclusion.

The result is shown in Table 4 which indicates that the conjugate (6~3) had a remarkable prohibiting effect on the proliferation of the target MM46 cells corresponding to the concentrations. The culture was carried out in two groups and the values show their averages.

TABLE 4

| Corresponding concentration of nitrosourea of conjugate (6~3) (μM) | Number of viable cells after 48 hours of culture ($\times 10^{-4}$/ml) |
| --- | --- |
| 0 | 41 |
| 0.1 | 40 |
| 1.0 | 33 |
| 10 | 12 |

EXAMPLE 7

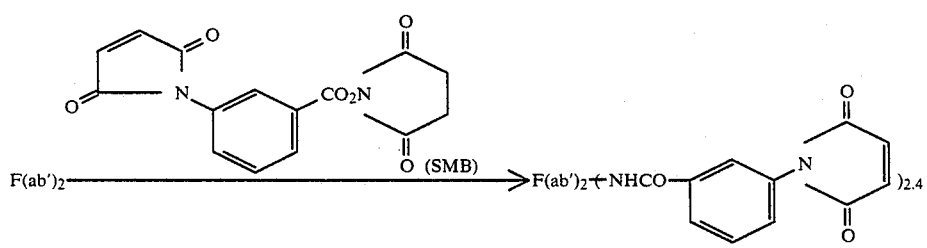

7~1

-continued

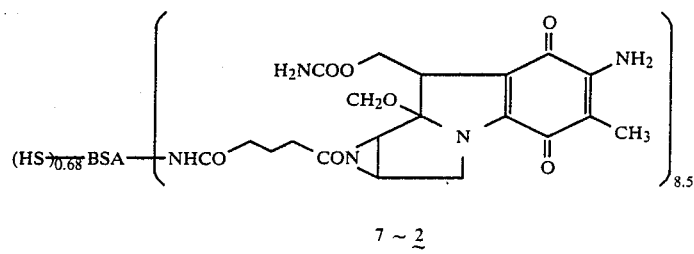

7 ~ 2

(7 ~ 1) + (7 ~ 2)

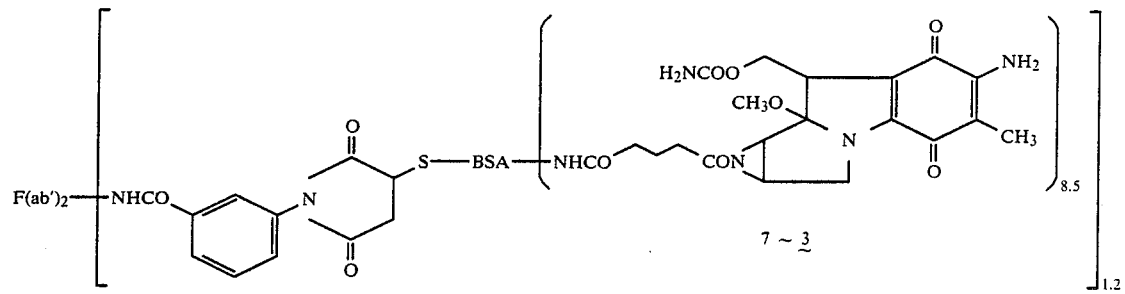

7 ~ 3

7-(a) Preparation of F(ab')₂ containing maleimide groups

20 μl of 100 mM DMF solution of SMB was added to 1.0 ml of 0.1M phosphate buffer—0.1M NaCl (pH 7.0) solution containing 20 mg of rabbit F(ab')₂ obtained in the aforementioned Referential example 1, 1-(b), at room temperature. When the mixture was stirred slowly for 30 minutes, it was, without losing time, passed through a column (1.0 cm × 30 cm) of Sephadex G-25 (0.1M phosphate buffer—0.1M NaCl, pH 6.5) to remove the low molecular weight substances, thus obtaining 6.7 ml of solution containing rabbit IgG reacted with SMB.

The quantity of protein of F(ab')₂ reacted with SMB (7 ~ 1) contained in the solution thus obtained was 16.1 mg when determined from the absorbance at 280 nm. The number of maleimide groups introduced into the F(ab')₂ molecule was 2.4 in average when determined according to the same method as in the case of IgG reacted with SMB in Example 2, 2-(a).

7-(b) Preparation of conjugate (7 ~ 3) by reaction between F(ab')₂ containing maleimide group (7 ~ 1) and BSA linked with MMC (7 ~ 2)

2.0 ml of a solution (0.1M phosphate buffer—0.1M NaCl, pH 6.5) of F(ab')₂ containing an average of 2.4 maleimide groups obtained in the preceding 7-(a) was mixed with 2.8 ml of a solution (0.01M AcONa—0.14M NaCl—0.01 mM EDTA, pH 5.25) containing 19 mg of BSA linked with an average of 8.5 MMC obtained according to Example 2, 2-(c), and the mixture was allowed to react overnight at 4° C. It was confirmed that the reaction product was mainly composed of conjugate (7 ~ 3) of F(ab')₂ bound to 1 to 2 BSA carrying MMC, when the reaction solution was examined by SDS electrophoresis. The conjugate was purified by use of a column (1.8 cm × 80 cm) of Sephadex G-150 super fine.

7-(c) Cytotoxicity of conjugate (7 ~ 3) against L 1210 cells

An experiment was made to examine the cytotoxicity of the conjugate (7 ~ 3) obtained in the preceding 7-(b) against the target L 1210 cells.

0.9 ml of RPMI 1640 culture medium (containing 10% calf serum, 20 μM 2-mercaptoethanol and 0.1 mg/ml of kanamycin) containing 5 × 10⁴ L 1210 cells was placed in wells of a 24-hole culture plate and 0.1 ml of subject samples diluted to varied concentrations were added thereto. The culture was carried out at 37° C. in an atmosphere of 5% $CO_2$ for 48 hours and the viable cells were counted by dye exclusion with Trypan Blue.

The result is shown in Table 5 indicating that the conjugate 7 ~ 3 had a remarkable effect of prohibiting the proliferation of the target L 1210 cells corresponding to the concentrations. The culture was carried out in two groups and the values show their averages.

TABLE 5

| Corresponding concentration of mitomycin of conjugate (7 ~ 3) | Number of viable cells after 48 hours of culture ( × $10^{-4}$/ml) |
| --- | --- |
| 0 | 45 |
| 0.1 | 42 |
| 1.0 | 33 |
| 10 | 6.1 |

EXAMPLE 8

An antitumor conjugate, comprising IgG and MMC-linked BSA bound to each other with their respective amino groups and thiol groups through the cross linking agent MCAE, was prepared according to Example 2, wherein MCAE was used in place of SMB which was used in Example 2.

EXAMPLE 9

An antitumor conjugate, in which IgG and HSA having nitrosourea linked thereto were bound to each other with their respective amino groups and thiol groups connected through the cross linking agent MCAE, was prepared according to Example 3, wherein MCAE was used in the place of SMB which was used in Example 3.

EXAMPLE 10

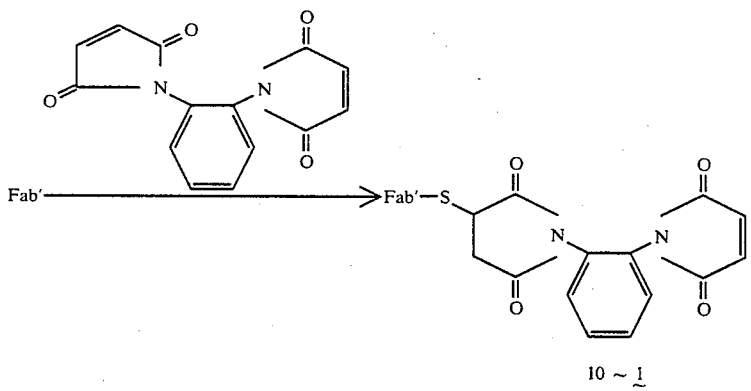

10~1

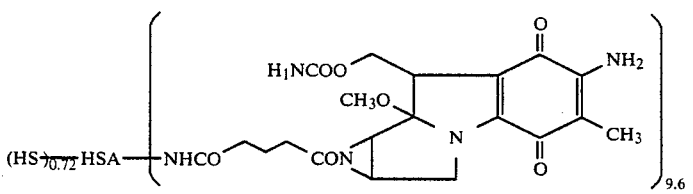

10~2

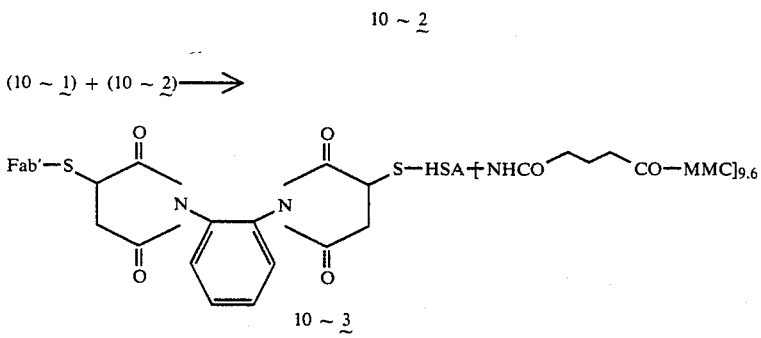

10~3

1.5 ml of solution (5 mM AcONa-0.14M NaCl, pH 5.5, hereinafter referred to as buffer A) containing 13.0 mg of fragment Fab' of rabbit IgG obtained in Referential Example 1, 1-(c), was admixed with 1.5 ml of a saturated solution (buffer A being used as a solvent) of N,N'-O-phenylenedimaleimide (hereinafter referred to as PDM) and the admixture was allowed to react at room temperature for 30 minutes. Then, the excess reagent was removed by Sephadex G-25 (0.8 cm×44 cm, buffer A) to obtain 8.6 ml of a solution containing Fab' having maleimide group expressed by formula 10~1.

Also, HSA having an average of 9.6 MMC linked thereto expressed by formula 10~2 was prepared according to the same method as Example 2, wherein HSA was used in the place of BSA. Incidentally, it was confirmed that said HSA contained 0.72 thiol group when determined according to Example 2. 2.0 ml of a solution (0.01M AcONA—0.14M NaCl—0.01 mM EDTA, pH 5.25) containing 7.9 mg of said MMC linked HSA was mixed with 2.0 ml of a solution of Fab' containing maleimide group expressed by the above-mentioned formula 10~1 and the mixture was made to react overnight at 4° C. Upon examination by SDS electrophoresis, it was ascertained that the reaction product contained the conjugate comprising Fab' and HSA linked thereto expressed by formula 10~3. The conjugate was purified with a column (1.5 cm×80 cm) of Sephadex G-150 super fine.

EXAMPLE 11

An antitumor conjugate, in which fragment Fab' and HSA having MMC linked thereto was bound to each other with their respective thiol groups through the cross linking agent BME

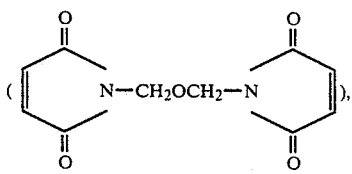

was obtained according to Example 10, wherein a cross linking agent N,N'-bis(maleimidemethyl)ether (hereinafter referred to as MBE) (see W. G. Freedberg, Journal of Biological Chemistry, Vol. 246, pp. 1449–1459, 1971) was used in the place of the cross linking agent PDM which was used in Example 10.

What is claimed is:

1. A conjugate having cytotoxicity prepared by covalently binding a serum albumin having a cytotoxic substance linked thereto to an immunoglobulin, or its fragment, which is able to selectively bind to a particular antigen of a cell to be killed,
wherein said immunoglobulin or its fragment is bound to said serum albumin by means of at least one sulfur atom, and wherein said serum albumin is linked to said cytoxic substance by an imino group.

2. The conjugate having cytotoxicity according to claim 1, wherein said serum albumin is a human or bovine serum albumin.

3. The conjugate having cytotoxicity according to claim 1, wherein the conjugate is expressed by the following formula (I)

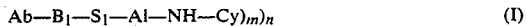
$$\text{Ab}-\text{B}_1-\text{S}_1-\text{Al}-\text{NH}-\text{Cy})_m)_n \quad (I)$$

wherein Ab indicates an immunoglobulin or its fragment, Al a serum albumin, and Cy a cytotoxic substance respectively; $S_1$ and NH indicate a sulfur atom and an imino group in the serum albumin respectively; $B_1$ indicates a divalent organic group; m indicates an integer 1 to 30 and n an integer 1 to 10 respectively.

4. The conjugate having cytotoxicity according any one of claims 1, 2, or 3, wherein the conjugate is expressed by the following formula (II)

$$\text{Ab}-(\text{B}_2)_{t_2}-\text{S}_2-(\text{B}_3)_{t_3}-\text{S}_1-\text{Al}-\text{NH}-\text{Cy})\text{m})_n \quad (II)$$

wherein Ab indicates a serum albumin; Cy indicates a cytotoxic substance; $S_1$ and NH indicate a sulfur atom or an imino group in the serum albumin respectively; m indicates an integer of 1 to 30; n indicates an integer of 1 to 10; $S_2$ indicates a sulfur atom; $B_2$ and $B_3$ indicate divalent organic groups; $t_2$ and $t_3$ are identical with or different from each other; being 1 or 1; providing that when $t_2$ equals 0, $S_2$ is a sulfur atom arising from the immunoglobulin or its fragment and when $t_2$ equals 1, $S_2$ is a sulfur atom introduced by a cross-linking agent.

5. The conjugate having cytotoxicity according to any one of claims 1, 2 or 3, wherein the conjugate is expressed by the following formula (III)

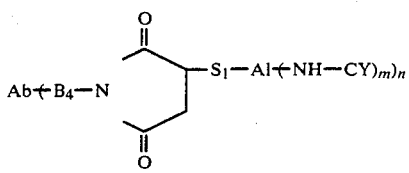

wherein Ab indicates an immunoglobulin or its fragment; Al indicates a serum albumin; Cy indicates a cytotoxic substance; $S_1$ and NH indicate a sulfur atom and an imino group in the serum albumin respectively; m indicates an integer of 1 to 30; n indicates an integer of 1 to 10; and $B_4$ indicates a divalent organic group.

6. A process for the preparation of a conjugate having cytotoxicity expressed by the following formula (II-1)

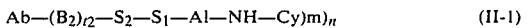
$$\text{Ab}-(\text{B}_2)_{t_2}-\text{S}_2-\text{S}_1-\text{Al}-\text{NH}-\text{Cy})\text{m})_n \quad (II\text{-}1)$$

wherein Ab indicates an immunoglobulin or its fragment; Al indicates a serum albumin; Cy indicates a cytotoxic substance; $S_1$ and NH indicate a sulfur atom and an imino group in the serum albumin respectively; m indicates an integer of 1 to 30; n indicates an integer of 1 to 10; $S_2$ indicates a sulfur atom; $B_2$ indicates a divalent organic group; and $t_2$ indicates 0 or 1, providing that when $t_2$ equals 0, $S_2$ is a sulfur atom arising from the immunoglobulin or its fragment and when $t_2$ equals 1, $S_2$ is a sulfur atom introduced by a cross-linking agent: characterized by covalently binding a serum albumin expressed by the following formula (V) having a group capable of forming an active disulfide group and having a cytotoxic substance linked thereto

$$\text{XS}_1-\text{Al}-\text{NH}-\text{Cy})\text{m} \quad (V)$$

wherein Al indicates a serum albumin; Cy indicates a cytotoxic substance; $S_1$ and NH indicate a sulfur atom and an imino group in the serum albumin respectively; m indicates an integer of 1 to 30; and X indicates a group which is capable of forming an active disulfide linkage with the neighboring sulfur atom;
with an immunoglobulin or its fragment expressed by the following (IV) having a generated or introduced thiol group

$$\text{Ab}-(\text{B}_2)_{t_2}-\text{S}_2\text{H})_{n'} \quad (IV)$$

wherein Ab indicates an immunoglobulin or its fragment; $S_2$ indicates a sulfur atom; $B_2$ indicates a divalent organic group; $t_2$ is 0 or 1; and n' is an integer of 1 to 10; providing that when $t_2$ equals 0, $S_2$ is a sulfur atom arising from the immunoglobulin or its fragments and when $t_2$ equals 1, $S_2$ is a sulfur atom introduced by a cross-linking agent.

7. A process for the preparation of a conjugate having cytotoxicity expressed by the formula (II-1)

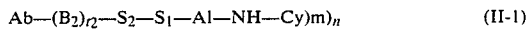
$$\text{Ab}-(\text{B}_2)_{t_2}-\text{S}_2-\text{S}_1-\text{Al}-\text{NH}-\text{Cy})\text{m})_n \quad (II\text{-}1)$$

wherein Ab indicates an immunoglobulin or its fragment; Al indicates a serum albumin; Cy indicates a cytotoxic substance; $S_1$ and NH indicate a sulfur atom and an imino group in the serum albumin respectively; m indicates an integer of 1 to 30; n indicates an integer of 1 to 10; $S_2$ indicates a sulfur atom; $B_2$ is a divalent organic group; and $t_2$ is 0 or 1; providing that when $t_2$ equals 0, $S_2$ is a sulfur atom arising from the immunoglobulin or its fragment and when $t_2$ equals 1, $S_2$ is a sulfur introduced by a cross-linking agent:
characterized by covalently binding a serum albumin expressed by the following formula (VII) having a cytotoxic substance linked thereto

$$\text{HS}_1-\text{Al}-\text{NH}-\text{Cy})\text{m} \quad (VII)$$

wherein Al represents a serum albumin; Cy represents a cytotoxic substance; $S_1$ and NH represent a sulfur atom and an imino group in the serum albumin respectively; and m indicates an integer of 1 to 30:
with an immunoglobulin or its fragment expressed by the following formula (VI) having an induced or introduced active disulfide group

$$\text{Ab}-(\text{B}_2)_{t_2}-\text{S}_2\text{X})_{n'} \quad (VI)$$

wherein Ab indicates an immunoglobulin or its fragment; $S_2$ indicates a sulfur atom; $B_2$ indicates a divalent organic group; $t_2$ is 0 or 1; n' is an integer of 1 to 10; and X represents a group which is capable of forming an active disulfide linkage with the neighboring sulfur atom; providing that when $t_2$ equals 0, $S_2$ is a sulfur atom arising from the immunoglobulin or its fragment and when $t_2$ equals 1, $S_2$ is a sulfur atom introduced by a cross-linking agent.

8. A process for the preparation of a conjugate having cytotoxicity expressed by the following formula (II-2)

$$Ab-(B_2)_{t_2}-S_2-B_3-S_1-Al-NH-Cy)m)_n \qquad (II-2)$$

wherein Ab indicates an immunoglobulin or its fragment; Al indicates a serum albumin; Cy indicates a cytotoxic substance; $S_1$ and NH indicate a sulfur atom and an imino group in the serum albumin respectively; m indicates an integer of 1 to 30; n indicates an integer of 1 to 10; $S_2$ indicates a sulfur atom; $B_2$ and $B_3$ are divalent organic groups; and $t_2$ is 0 or 1, providing that when $t_2$ equals 0, $S_2$ is a sulfur atom arising from the immunoglobulin or its fragment and when $t_2$ equals 1, $S_2$ is a sufur atom introduced by a cross-linking agent:

characterized by covalently binding a serum albumin, which has a cytotoxic substance linked thereto, expressed by the formula (VII)

$$HS_1-Al-NH-Cy)m \qquad (VII)$$

wherein Al indicates a serum albumin; Cy indicates a cytotoxic substance; $S_1$ and NH indicate a sulfur atom and an imino group in the serum albumin respectively; and m indicates an integer of 1 to 30:

to an immunoglobulin or its fragment, which has a generated or introduced thiol group, expressed by the formula (IV)

$$Ab-(B_2)_{t_2}-S_2H)_{n'} \qquad (IV)$$

wherein Ab indicates an immunoglobulin or its or its fragment; $S_2$ indicates a sulfur atom; $B_2$ is a divalent organic group; $t_2$ is 0 or 1; and $n'$ is an integer of 1 to 10; providing that when $t_2$ equals 0, $S_2$ is a sulfur atom arising from the immunoglobulin or its fragment and when $t_2$ equals 1, $S_2$ is a sulfur atom introduced by a cross-linking agent:

with the use of a cross-linking agent having two functional groups which are capable of reacting with a thiol group.

9. A process for the preparation of a conjugate having cytotoxicity expressed by formula (III)

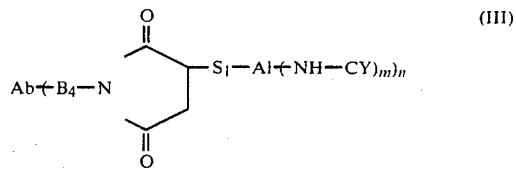

wherein Ab represents an immunoglobulin or its fragment; Al represents a serum albumin; Cy represents a cytotoxic substance; $S_1$ and NH represent a sulfur atom and an imino group in the serum albumin respectively; m represents an integer of 1 to 30; n represents an integer of 1 to 10; and $B_4$ represents a divalent organic group:

characterized by covalently binding a serum albumin, which has a cytotoxic substance linked thereto, expressed by the formula (VII)

$$HS_1-Al-NH-Cy)m \qquad (VII)$$

wherein Al represents a serum albumin; Cy represents a cytotoxic substance; $S_1$ and NH represent a sulfur atom and an imino group in the serum albumin respectively; and m represents an integer of 1 to 30:

with an immunoglobulin or its fragment, which has an introduced maleimide group, expressed by the following formula (VIII)

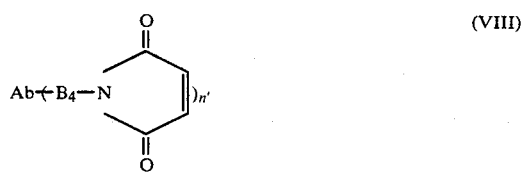

wherein Ab represents an immunoglobulin or its fragment; $n'$ represents an integer of 1 to 10; and $B_4$ represents a divalent organic group.

10. The conjugate having cytotoxicity according to claim 2, wherein the conjugate is expressed by the following formula (I)

$$Ab-B_1-S_1-Al-NH-Cy)m)_n \qquad (I)$$

wherein Ab indicates an immunoglobulin or its fragment, Al a serum albumin, and Cy a cytotoxic substance respectively; $S_1$ and NH indicate a sulfur atom and an imino group in the serum albumin respectively; $B_1$ indicates a divalent organic group; m indicates an integer 1 to 30 and n an integer 1 to 10 respectively.

* * * * *